United States Patent [19]

Saitoh et al.

[11] Patent Number: 5,234,972
[45] Date of Patent: Aug. 10, 1993

[54] DENTAL ADHESIVE COMPRISING AN ITACONIC ACID MONOESTER COMPOUND

[75] Inventors: Yoshihiro Saitoh, Neyagawa; Kazusato Kanda, Moriguchi; Kimio Fukuda, Hirakata, all of Japan

[73] Assignee: Ube Industries, Ltd., Ube, Japan

[21] Appl. No.: 598,700

[22] PCT Filed: Feb. 13, 1990

[86] PCT No.: PCT/JP90/00172

§ 371 Date: Oct. 12, 1990

§ 102(e) Date: Oct. 12, 1990

[87] PCT Pub. No.: WO90/09365

PCT Pub. Date: Aug. 23, 1990

[30] Foreign Application Priority Data

Feb. 14, 1989 [JP] Japan ................... 1-34488

[51] Int. Cl.$^5$ .................. C08K 5/10; C08F 20/68; C07C 69/52; C07C 69/66; A61K 6/08
[52] U.S. Cl. .................... 523/118; 526/318; 526/318.2; 560/185; 560/190; 560/198
[58] Field of Search ........ 526/318, 318.1, 318.2; 523/116, 118, 120; 560/185, 198, 190

[56] References Cited

U.S. PATENT DOCUMENTS 4,812,549 3/1989 Muramoto et al. ............ 526/318

FOREIGN PATENT DOCUMENTS

| | | |
|---|---|---|
| 53-39331 | 4/1978 | Japan . |
| 53-144939 | 12/1978 | Japan . |
| 54-21438 | 2/1979 | Japan . |
| 57-75907 | 5/1982 | Japan . |
| 58-17513 | 4/1983 | Japan . |
| 58-173175 | 10/1983 | Japan . |
| 59-30681 | 7/1984 | Japan . |
| 60-45510 | 5/1985 | Japan . |
| 60-202873 | 10/1985 | Japan . |
| 61-176507 | 8/1986 | Japan . |
| 62-161709 | 7/1987 | Japan . |
| 279782 | 6/1988 | Japan . |

OTHER PUBLICATIONS

Dental Materials and Devices (Shika Zairyo-Kikai) vol. 8, No. 3, pp. 307-323 (1989); "Studies on Adhesion of Dental Resin to Tooth Structure-Syntheses and Adhesion to Tooth Structure of Various Aliphatic Methacrylates with a Carboxylic Group".

*Primary Examiner*—Paul R. Michl
*Assistant Examiner*—Tae H. Yoon
*Attorney, Agent, or Firm*—Armstrong, Westerman, Hattori, McLeland & Naughton

[57] ABSTRACT

A novel itaconic acid monoester compound represented by the following general formula (1)

$$CH_2=\overset{R_1}{\underset{|}{C}}-COO-R_2-OCO-CH_2-\overset{CH_2}{\underset{\|}{C}}-COOH \quad (1)$$

($R_1$ represents —H or —$CH_3$, and $R_2$ represents a $C_2$–$C_{10}$ alkylene group, an oxyethylene group or a derivative thereof).

The above compound is ordinarily synthesized from itaconic anhydride and a hydroxyalkyl ester of (meth)acrylic acid.

Further, the above compound has hydrophilic groups and hydrophobic groups in appropriate balance, is superior in hardness, compression strength and water absorbability, and is suitable for use particularly in a dental adhesive comprising the compound or a polymer thereof. When the compound is used in a dental adhesive, the dental adhesive shows strong adhesion to the teeth or a composite resin over a long period even under a wet condition inside the mouth, and has excellent durability.

9 Claims, 1 Drawing Sheet

DENTAL ADHESIVE COMPRISING AN ITACONIC ACID MONOESTER COMPOUND

TECHNICAL FIELD

The present invention relates to a novel itaconic acid monoester compound and a dental adhesive comprising said compound. More particularly, the present invention relates to a dental adhesive used as a self-adhesive dental filler, an adhesive resin cement, an orthodontic adhesive and the like, or used for enhancing the adhesion between the teeth and a filler (e.g. ordinary composite resin), a dental material or the like.

BACKGROUND ART

In recent years, composite resins have been developed for the treatment of carious teeth, as a replacement for dental cements such as zinc phosphate cement, silic acid cement and the like, and there have recently been produced composite resins showing stable water absorbability and low disintegratability over a long period and having substantially the same color tone as natural teeth. Composite resins, however, do not essentially adhere to the enamel and dentin of the teeth; therefore, during the long use of the composite resin, a gap is formed between the tooth and the composite resin used as a filler, secondary caries tend to arise, and in some cases the composite resin was detached. There have heretofore been developed various adhesion improvers such as adhesive liner and the like, for improvement of the adhesion between the composite resin and the cavity wall, and further there have been proposed dental adhesive compositions having adhesivity to the tooth, such as adhesive filler for prevention of caries, orthodontic adhesive and the like.

However, only part of these conventional products maintains strong adhesion to the teeth over a long period in a circumstance (e.g. inside the mouth) which is wet and shows severe temperature change. For example, there was developed an adhesive composed mainly of an α-cyanoacrylate, to use as a filler for prevention of caries and an orthodontic adhesive both having adhesivity to the teeth. However, the adhesive is said to have problems in durability inside the mouth as well as in handleability during use.

Meanwhile, in recent years there has been widely used a filler which uses a resin composed mainly of bisphenol A diglycidyl methacrylate and wherein the resin is to be cured with a benzoyl peroxide-amine type catalyst. This filler, however, has no adhesion to the dentin and the enamel, therefore, when filled in dental cavities, is detached after a little while and induces the formation of secondary caries.

Also, an adhesive comprising 2-methacryloyloxyethyltrimellitic acid anhydride has been proposed as an adhesive having excellent water resistance and durability and well withstanding the inside-the-mouth use. However, the catalyst for normal temperature polymerization, used in the adhesive is ordinarily restricted virtually to tri-n-butylborane oxide; therefore, the adhesive, although having strong adhesion to the dentin of the teeth, is slow in polymerization reaction rate, requires ten and odd minutes up to the completion of curing, is very unstable in the air making its handling difficult; thus, the adhesive has many problems from the standpoint of clinical dentistry.

As described above, there has been found yet no dental material having adhesion to both the dentin and the enamel and maintaining strong adhesion over a long period even in an inside-the-mouth circumstance which is wet and shows severe temperature change.

In view of the above prior art, the present invention is intended to provide a dental adhesive which has physical and engineering properties required for dental adhesives, for example, hardness, compression strength, water resistance, etc. and which further has excellent adhesion to the dentin and the enamel.

DISCLOSURE OF THE INVENTION

According to the present invention there are provided an itaconic acid monoester compound represented by the following general formula (1)

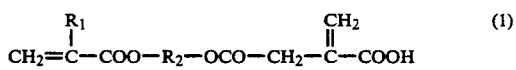

($R_1$ represents —H or —$CH_3$, and $R_2$ represents a $C_2$~$C_{10}$ alkylene group, an oxyethylene group or a derivative thereof), and a dental adhesive comprising said itaconic acid monoester compound or a polymer thereof.

The itaconic acid monoester compound of the present invention is a novel compound and has hydrophilic groups and hydrophobic groups in appropriate balance; therefore, the compound is superior in physical properties required for dental adhesives, for example, hardness, compression strength, water absorbability, etc.

Further, the adhesive comprising the itaconic acid monoester compound of the present invention can retain high adhesion even in water or saliva over a long period because the polymer of the itaconic acid monoester compound represented by the formula (1) has good adhesion to the teeth. Therefore, the adhesive has good durability in the mouth and, even when used as a filler, can adhere strongly to the dentin over a long period in an in-the-mouth circumstance which is wet and shows severe temperature change. Further, the adhesive, when used as an undercoat for composite resin, orthodontic adhesive, etc., shows strong adhesion not only to the teeth but also to the composite resin, the orthodontic adhesive, etc. Accordingly, the gap which has existed between the dentin and the composite resin, the orthodontic adhesive or the like can be filled without fail; also, marginal closure is improved; resultantly, secondary caries can be prevented completely.

Furthermore, the adhesive can also be utilized as a resin cement which is insoluble in saliva and has adhesivity, in place of the zinc phosphate cement used for bonding a restorative material to an abutment tooth.

The present invention is described in more detail below.

The compound represented by the above general formula (1) is a novel compound, and is synthesized ordinarily from itaconic anhydride and a hydroxyalkyl (meth)acrylate as shown in the following formula (2).

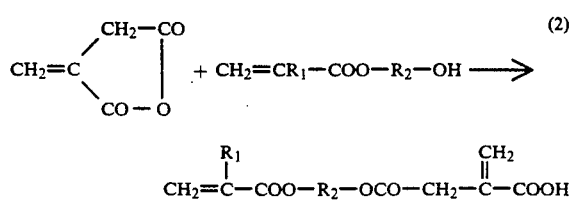

The synthesis is generally effected by subjecting materials, i.e. a substantially equimolar mixture of itaconic anhydride and a hydroxyalkyl (meth)acrylate to a reaction with heating and stirring at a temperature of 50°–70° C.

The obtained itaconic acid monoester compound shows the wave numbers ($\nu_{max}$) 1720 and 1770 cm$^{-1}$ of the infrared absorption spectrum (hereinafter referred to as IR) of carbonyl group characterizing itaconic acid, and moreover the IR wave number ($\nu_{max}$) 1640 cm$^{-1}$ of (meth)acryloyl group and the IR wave number ($\nu_{max}$) 1170 cm$^{-1}$ of oxyalkyl group. Therefore, the compound clearly has a (meth)acryloyl group and an oxyalkyl group in the molecule. The more detailed structure of the compound can be identified by its nulcear magnetic resonance spectrum (NMR).

The itaconic acid monoester compound of the present invention obtained by the above process is useful as a dental adhesive and, besides, can be utilized also as an industrial adhesive, a thermosetting coating, a paper processing agent, a lube additive, a textile oil (for antistatic purpose, etc.) a flame retardancy-imparting agent, a solvent for metal adhesion, a metal extracting agent, etc.

The dental adhesive comprising the itaconic acid monoester compound represented by the general formula (1) or a polymer thereof may comprise the itaconic acid monoester compound as a polymerizable monomer, alone or together with other polymerizable monomer, or may comprise a homopolymer of the itaconic acid monoester or a copolymer of the itaconic acid monoester and other polymerizable monomer, or may comprise a mixture of these polymers and other polymerizable monomer. Ordinarily, the dental adhesive is cured at the time of use, whereby the adhesive is allowed to adhere to the teeth.

The dental adhesive of the present invention is characterized by being an itaconic acid monoester represented by the formula (1), and exhibits excellent adhesion to the dentin while maintaining adhesion to the enamel with the actions of the itaconic acid residue and other functional groups possessed by the itaconic acid monoester compound. The reason for the excellent adhesion to the dentin is presumed to be that the hydrophilic groups and hydrophobic groups of the itaconic acid monoester compound of the formula (1) are well balanced and favorably arranged with respect to the affinity to the organic substances (e.g. collagen) of teeth.

As the compound represented by the formula (1), useful for use in the dental adhesive of the present invention, there can be mentioned, for example, the following compounds ① to ⑪.

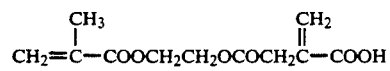

(1)

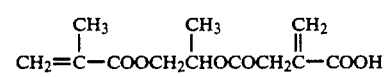

(2)

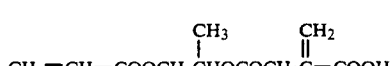

(3)

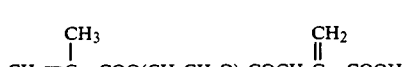

(4)

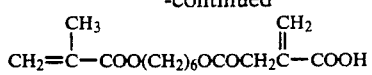

(5)

(6)

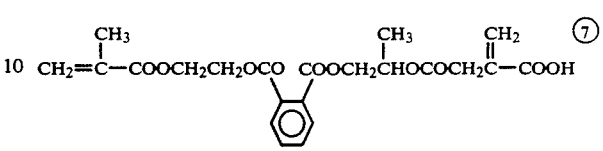

(7)

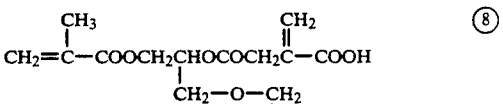

(8)

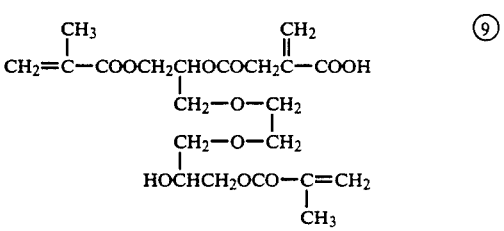

(9)

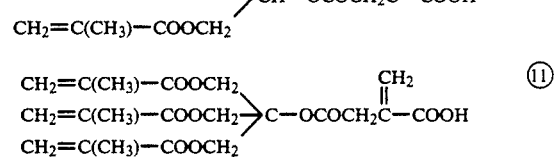

(10)

$$CH_2=C(CH_3)-COOCH_2$$
$$CH_2=C(CH_3)-COOCH_2 \!\!\rightarrow\!\! C-OCOCH_2\overset{CH_2}{\underset{\|}{C}}-COOH$$
$$CH_2=C(CH_3)-COOCH_2$$

(11)

The dental adhesive of the present invention can comprise, besides the above-mentioned components, known components used ordinarily, depending upon the type of adherend and the purpose of use.

For example, when the dental adhesive is used as an adhesive filler, the dental adhesive comprises, as a polymerizable monomer, only an itaconic acid monoester compound of the formula (1) and, at the time of use, is polymerized and cured in the presence of a curing agent; thus, the adhesive is used as an adhesive filler. Ordinarily, however, a mixture of an itaconic acid monoester compound of the formula (1) and other polymerizable monomer is used as a polymerizable monomer, and at the time of use, the mixture is polymerized and cured in the presence of a curing agent. In this case, the other polymerizable monomer can be methyl methacrylate, hydroxyethyl methacrylate, ethylene glycol dimethacrylate, di- or tri- or tetraethylene glycol dimethacrylate, glycidyl methacrylate, 2,2'-bis(methacryloxyphenyl)propane, 2,2'-bis[4-(3-methacryloxy)-2-hydroxypropoxylphenyl]propane, styrene, 1,3-butanediol dimethacrylate, tetrahydrofurfuryl methacrylate, trimethacrylic acid trimethylolpropane, bis(oxyethylated bisphenol A) dimethacrylate, etc.

The dental adhesive may further comprise, as necessary, a polymer and/or an oligomer both of a polymerizable monomer including an itaconic acid monoester compound of the formula (1), for the adjustment of the viscosity, curing rate, polycondensation, etc. The dental adhesive may furthermore comprise desired additives, for example, an inorganic filler preferably having particle diameters of 100 μm or less (e.g. silica, glass beads, alumina, quartz powder), an inorganic filler treated with a silane coupling agent (e.g. γ-methacryloxypropyltrimethoxy-silane, vinyltrichlorosilane, vinyltriethoxysilane) for improvement of bondability to resin, a curing agent, a polymerization inhibitor, a coloring agent, an antioxidant and an ultraviolet absorber.

When there is used a combination of two curing agents, for example, an amine and a peroxide, or a p-toluenesulfinic acid salt and a peroxide, it is preferable that the itaconic acid monoester compound of the formula (1) as a polymerizable monomer be divided into two equal portions, that one portion be mixed with a curing agent such as amine, p-toluenesulfinic acid salt or the like, and that the other portion be mixed with a curing agent such as peroxide or the like. When the itaconic acid monoester compound of the formula (1) is used as a mixture with other polymerizable monomer, it is preferable that the other polymerizable monomer be divided into two equal portions, that each of the two equal portions be mixed with either of the two curing agents, and that the itaconic acid monoester compound of the formula (1) be added to either one or both of the two polymerizable monomer portions each mixed with a different curing agent. These curing agents are mixed ordinarily at the time of use.

The amount of the itaconic acid monoester compound of the formula (1) used is not particularly restricted; however, it is 10-100% (% by weight, the same applies hereinafter), preferably 20-90% based on other polymerizable monomer when the compound of the formula (1) is used together with the other polymerizable monomer. When the amount is less than 10%, the adhesion is low, which is not preferable. The amount of the polymerizable monomer used is preferably 10-45% based on the whole adhesive composition, and the amount of the inorganic filler used is preferably 55-85% based on the whole adhesive composition.

When the dental adhesive of the present invention is used as an adhesive between a tooth (or teeth) and a filler (e.g. conventional composite resin) or the like, the adhesive can be used in a form that an itaconic acid monoester compound of the formula (1) is contained in an organic solvent such as ethyl ether, chloroform or the like, in an amount of 5-50%. Alternatively, the itaconic acid monoester compound of the formula (1) may be contained in the above-mentioned other polymerizable monomer in an amount of 5-50%. Also, the adhesive can be used in the same manner as when used as a filler as mentioned above.

When the dental adhesive of the present invention is used as a filler, the adhesive is filled into a cavity to be filled and is then cured. When the adhesive is used for adhesion between a dental filler and a tooth (or teeth), the adhesive is used, for example, by, after the formation of a cavity, coating the adhesive on the wall of the cavity, then filling the cavity with said dental filler, and effecting curing.

BEST MODE FOR CARRYING OUT THE INVENTION

Figure 1:
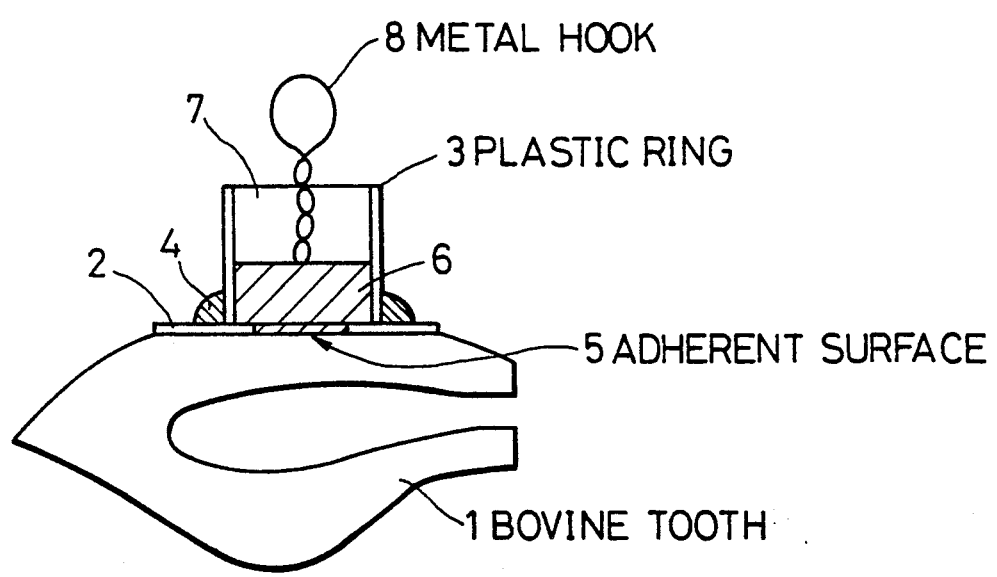
FIG. 1 is a sectional view of a bovine tooth for test purpose, used for measuring the adhesivity of a compound of the present invention.

The present invention is described in detail below referring to Examples. However, the present invention is not restricted to these Examples.

Incidentally, the analysis and measurements of synthesized compounds, etc. in the present Examples were made by the following methods.

[1] Elemental analysis (EA)

Carbon and hydrogen were measured by Elemental Analyzer 240 manufactured by Perkin Elmer.

[2] Infrared absorption spectrum (IR)

Measured by infrared absorption spectrography by Model 1750 manufactured by Perkin Elmer, according to a liquid film method using a sodium chloride plate.

[3] Nuclear magnetic resonance spectrum (NMR)

Measured by NMR Analyzer GX-270 manufactured by Nihon Denshi K.K., using deuterated chloroform as a solvent and tetramethylsilane as a reference material.

EXAMPLE 1

The compound ① $CH_2=C(CH_3)COOCH_2CH_2OCOCH_2C(=CH_2)-COOH$ was synthesized.

A mixture of 29.0 g of 2-hydroxyethyl methacrylate (hereinafter referred to as HEMA) and 25.0 g of itaconic anhydride was subjected to a reaction at 60° C. for 24 hours with heating and stirring.

After the reaction, the reaction mixture was allowed to cool. Thereto was added 450 ml of a 5% aqueous sodium carbonate solution to obtain an aqueous solution. The aqueous solution was washed four times each with 125 ml of ethyl ether. After the washing, the aqueous solution was mixed with 5% hydrochloric acid until the resulting mixture had a pH 3-4. The oily matter was separated from the aqueous layer. The oily matter was extracted with 250 ml of ethyl acetate. The extract was washed with distilled water, and then dehydrated with sodium sulfate for 24 hours. Thereafter, ethyl acetate was removed by distillation under reduced pressure to obtain 38.2 g of an oily matter.

The analytical results for the oily matter were as follows.

EA (%): C 54.45, H 5.95. Theoretical: C 54.54, H 5.83.

NMR (CDCl$_3$), δ (ppm): 9.25 (bs 1H;—COOH), 6.45, 5.85 (d 2H;CH$_2$=C(—COOH)—), 6.15, 5.60 (d 2H;CH$_2$=C(—CH$_3$)—), 4.35 (s 4H;—OCH$_2$CH$_2$O—), 3.35 (s 2H;—C(=O)—CH$_2$—), 1.95 (s 3H;—CH$_3$).

IR $\nu_{max}$ (cm$^{-1}$): 1770, 1720, 1640, 1160

EXAMPLE 2

The compound ② $CH_2=C(CH_3)COOCH_2CH(CH_3)OCOCH_2C(=CH_2)-COOH$ was synthesized by reacting itaconic anhydride and hydroxyisopropyl methacrylate in the same manner as in Example 1. The analytical results for the compound were as follows.

EA (%): C 56.01, H 6.37. Theoretical: C 56.24, H 6.29.

NMR (CDCl$_3$), δ (ppm): 10.50 (bs 1H;—COOH) 6.45, 5.85 (d 2H;CH$_2$=C(—COOH)—), 6.10, 5.55 (d 2H;CH$_2$=C(—CH$_3$)—), 5.20 (m 1H;—CH$_2$CH(—CH$_3$)—), 4.20 (m 2H;—CH$_2$CH(—CH$_3$)—), 3.35 (s 2H;—C(=O)—CH$_2$—), 1.95 (s 3H;CH$_2$=C(—CH$_3$)—), 1.30 (d 3H;—CH$_2$CH(—CH$_3$)—).

IR $\nu_{max}$ (cm$^{-1}$): 1770, 1720, 1640, 1170.

EXAMPLE 3

The compound ⑦ was synthesized by reacting itaconic anhydride and the following compound ⑫ in the same manner as in Example 1.

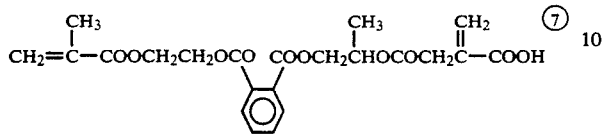

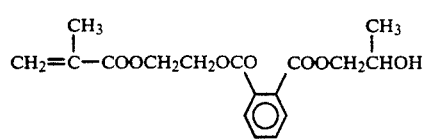

The analytical results for the compound ⑦ were as follows.

EA (%): C 58.77, H 5.50. Theoretical: C 58.93, H 5.39.

NMR (CDCl$_3$), δ (ppm): 8.75 (bs 1H;—COOH), 6.40, 5.80 (d 2H;CH$_2$=C(—COOH)—), 7.70, 7.55 (d 4H;

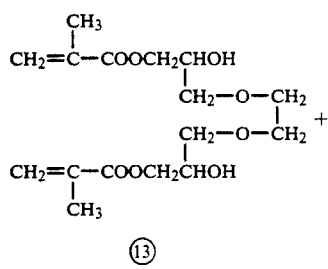

6.15, 5.60 (d 2H;CH$_2$=C(—CH$_3$)—), 5.30 (m 1H;—CH$_2$CH(—CH$_3$)—), 4.55, 4.45 (d 4H;—OCH$_2$C-H$_2$O—), 4.30 (m 2H;—CH$_2$CH(—CH$_3$)—), 3.35 (s 2H;—C(=O)—CH$_2$—), 1.95 (s 3H;CH$_2$=C(—CH$_3$)—), 1.30 (bs 3H;—CH$_2$CH(—CH$_3$)—)

IR ν$_{max}$ (cm$^{-1}$): 1770, 1720, 1640, 1170.

EXAMPLE 4

The compound ⑧ was synthesized by reacting itaconic anhydride with the following compound ⑬ in the same manner as in Example 1.

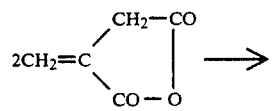

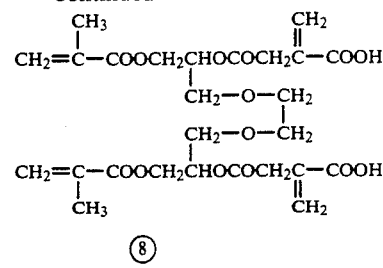

The analytical results for the compound ⑧ were as follows.

EA (%): C 54.55, H 6.19. Theoretical: C 54.73, H 6.01.

NMR (CDCl$_3$), δ (ppm): 7.85 (bs 2H; —COOH), 6.40, 5.80 (d 4H;CH$_2$=C(—COOH)—), 6.15, 5.60 (d 4H;CH$_2$=C(—CH$_3$)—), 5.30 (m 2H;

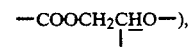

4.40 (m 4H;

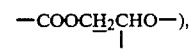

3.70 (m 8H;—CH$_2$OCH$_2$CH$_2$OCH$_2$—), 3.35 (s 4H;—C(=O)—CH$_2$—), 1.95 (s 6H;—CH$_3$).

IR ν$_{max}$ (cm$^{-1}$): 1770, 1720, 1640, 1170.

EXAMPLE 5

The compound ⑩ (CH$_2$=C(CH$_3$)—COOCH$_2$)$_2$CH-OCOCH$_2$C(=CH$_2$—COOH was synthesized by reacting itaconic anhydride with 2-hydroxy-1,3-dimethacryloxypropane in the same manner as in Example 1. The analytical results for the compound ⑩ were as follows.

EA (%): C 57.68, H 7.21. Theoretical: C 57.89, H 7.07.

NMR (CDCl$_3$), δ (ppm): 9.35 (bs 1H;—COOH), 6.45, 5.80 (d 2H;CH$_2$=C(—COOH)—), 6.10, 5.60 (d 4H;CH$_2$=C(—CH$_3$)—), 5.40 (m 1H;—CH$_2$—CH—CH$_2$—), 4.40 (m 4H;—COOCH$_2$—), 3.35 (s 2H;—C(=O)—CH$_2$—), 1.95 (s 6H;—CH$_3$).

IR ν$_{max}$ (cm$^{-1}$): 1770, 1720, 1640, 1170.

EXAMPLE 6

Preparation of adhesive

A two-part adhesive was prepared using a solution A consisting of 40% of the compound ① obtained in Example 1, 10% of HEMA, 49% of bis-oxyethylated bisphenol A dimethylacrylate represented by the following formula ⑭ and 1% of benzoyl peroxide (hereinafter referred to as BPO) and a solution B which is an ethanol solution containing 2% of sodium p-toluenesulfinate.

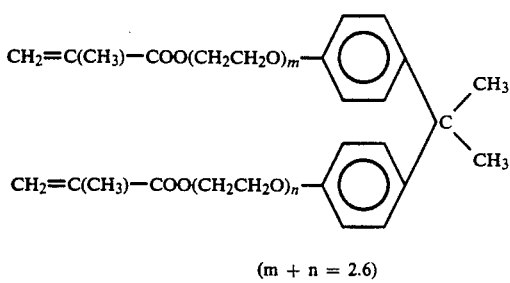

$CH_2=C(CH_3)-COO(CH_2CH_2O)_m$ ─⟨⟩
$CH_2=C(CH_3)-COO(CH_2CH_2O)_n$ ─⟨⟩
(14)
C(CH_3)(CH_3)

(m + n = 2.6)

Adhesion between dentin and composite resin

A tooth for test purpose was prepared by extracting a bovine tooth from a bovine mandibula right after slaughter which contained teeth, removing the tissue surrounding the tooth, and cutting off the corona dentis and radix dentis of the tooth with a diamond cutter (Maruto Cutter MC-100) to remove the pulpa dentis of the corona dentis. The resulting tooth for test purpose was stored in a refrigerator and thawed at the time of use.

The method for adhesion and the test method for adhesion strength used are explained in detail below, based on the case shown in FIG. 1.

A bovine tooth dentin was polished with water-resistant silicon papers (from coarse paper to #600), using Ecomet III (a product of Buehler) while pouring water; the polished dentin was subjected to etching by 65% phosphoric acid for 30 seconds; the resulting dentin was water-washed for 30 seconds to prepare a bovine tooth for test purpose.

In FIG. 1, to the bovine tooth 1 prepared as above was attached a cellophane tape 2 having a hole of 4 mm in diameter, whereby an area to be subjected to adhesion was specified. On the cellophane tape 2 was fixed a plastic ring 3 of 6 mm in inside diameter and 5 mm in height, using a parrafin wax 4.

Then, an adhesive which was an equal-volume mixture of the solution A and the solution B both prepared above, was coated on the surface 5 to be subjected to adhesion, in one layer. The ethanol in the adhesive was evaporated by an air gun. Then, a photopolymerizable composite resin, Pyrofil Light Bond Anterior Universal ® (a product of Sankin Kogyo K.K.) was packed in the plastic ring 3 up to a height of about 2 mm and subjected to light exposure by a light exposure apparatus, Suncure Light ® (a product of Sankin Kogyo K.K.) for 30 seconds to form a filler layer 6. Further on the filler layer 6 was placed a chemically polymerizable composite resin, Pyrofil Bond Anterior ® (a product of Sankin Kogyo K.K.) to form a filler layer 7. Before the filler layer 7 was cured, a metal hook 8 was fixed inside therein. After 10 minutes, the whole system was immersed in water of 37° C. for 24 hours. Then, the bovine tooth for test purpose was taken out and subjected to a tensile test to measure the adhesion strength. The tensile test was conducted by allowing Autograph DDS-500 (a tensile tester manufactured by Shimadzu Corp.) to hold the bovine tooth 1 and the metal hook 8 and measuring an adhesion strength between the bovine dentin 1 and the photopolymerizable composite resin filler layer 6 at a cross head speed of 2.0 mm/min. In this case, the photopolymerizable composite resin filler layer 6 and the chemically polymerizable composite resin filler layer 7 adhere strongly to each other; therefore, there occurs no breakage at the boundary of the two layers. Nor takes place the detachment of the metal hook 8 from the filler layer 7.

The adhesion strength was taken as an average of the tensile test results for the 8 bovine teeth for test purpose prepared as above, and was 52 kg/cm².

COMPARATIVE EXAMPLE 1

A bovine tooth for test purpose was prepared in the same manner as in Example 6 except that no adhesive of the present invention was used and a bovine tooth was allowed to adhere directly to the photopolymerizable composite resin. The bovine tooth was measured for adhesion strength in the same manner as in Example 6. The adhesion strength was 0 kg/cm².

COMPARATIVE EXAMPLE 2

Adhesion strength was measured in the same manner as in Example 6 except that there was used, as the solution A, a composition consisting of 10% of HEMA, 89% of the compound (14) and 1% of BPO. The adhesion strength was 0 kg/cm².

EXAMPLE 7

Adhesion strength was measured in the same manner as in Example 6 except that there was used, as the solution A, a composition consisting of 89% of the compound (1), 10% of HEMA and 1% of BPO. The adhesion strength was 42 kg/cm².

EXAMPLE 8

Adhesion of enamel and composite resin

Adhesion strength was measured in the same manner as in Example 6 except that a bovine tooth enamel was used in place of the bovine tooth dentin. The adhesion strength was 187 kg/cm².

EXAMPLE 9

Adhesion between Co-Cr alloy and composite resin

Adhesion strength was measured in the same manner as in Example 6 except that a Co-Cr alloy, Suncolium Hard (a product of Sankin Kogyo K.K.) was used in place of the bovine tooth dentin. The adhesion strength was 161 kg/cm².

Incidentally, the Co-Cr alloy was subjected to the following pretreatment. That is, the alloy was polished with water-resistant silicon carbide papers (up to #800) while pouring water, as in Example 6, then subjected to a sand blasting treatment, and subjected to ultrasonic cleaning in acetone for 5 minutes.

EXAMPLES 10-13

Adhesives were prepared in the same manner as in Example 6 except that in the preparation of a solution A, there were used the compounds (2), (7), (8) and (10) in place of the compound (1).

Using these adhesives, there were measured adhesion strengths between composite resin and bovine tooth dentin, bovine tooth enamel or Co-Cr alloy, in the same manners as in Examples 6, 8 and 9. The results were shown in Table 1.

TABLE 1

| Example | 10 | 11 | 12 | 13 |
|---|---|---|---|---|
| Compound in solution A | (2) | (7) | (8) | (10) |
| Adhesion strength (kg/cm²) | | | | |

TABLE 1-continued

| Example | 10 | 11 | 12 | 13 |
|---|---|---|---|---|
| Bovine tooth dentin | 38 | 24 | 42 | 32 |
| Bovine tooth enamel | 219 | 161 | 210 | 165 |
| Co—Cr alloy | 135 | 140 | 151 | 141 |

INDUSTRIAL APPLICABILITY

The above itaconic acid monoester compound of the present invention is useful as a dental adhesive and a dental filler, and besides, can be used in an industrial adhesive, a thermosetting coating, a paper processing agent, a lube additive, a textile oil (for antistatic purpose, etc.), a flame retardancy-imparting agent, a solvent for metal adhesion, a metal extracting agent, etc.

We claim:

1. A dental adhesive comprising an itaconic acid monoester compound represented by the general formula (1)

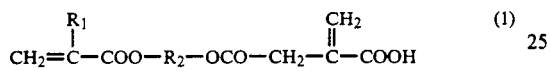

($R_1$ represents —H or $CH_3$, and $R_2$ represents a $C_2$-$C_{10}$ alkylene group, an oxyethylene group, or a polymer thereof, in an amount effective to improve the adhesion of said composition to bovine tooth dentin, and a curing agent.

2. A dental adhesive according to claim 1, wherein the general formula (1) is either of the following chemical formulas ① to ⑪.

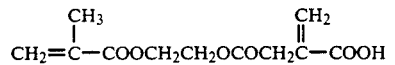

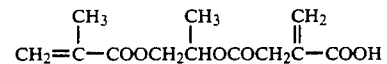

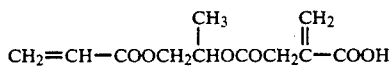

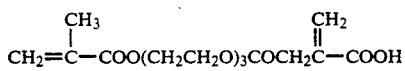

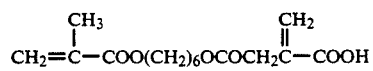

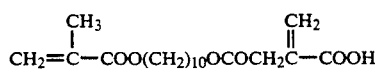

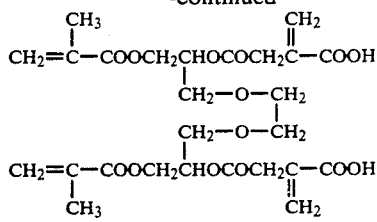

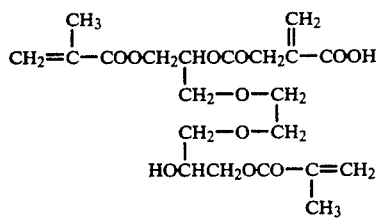

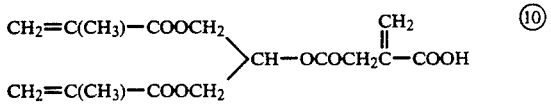

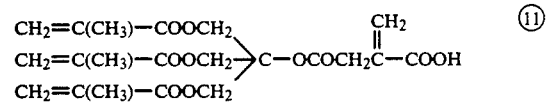

3. A dental adhesive according to claim 1 or 2, further comprising a polymerizable monomer.

4. A dental adhesive according to claim 3, wherein the polymerizable monomer is at least one member selected from methyl methacrylate, hydroxyethyl methacrylate, ethylene glycol dimethacrylate, di- or tri- or tetraethylene glycol dimethacrylate, glycidyl methacrylate, 2,2'-bis(methacryloxy-phenyl)propane, 2,2'-bis[4-(3-methacryloxy)-2-hydroxypropoxy-phenyl]propane, styrene, 1,3-butanediol dimethacrylate, tetrahydrofurfuryl methacrylate, trimethacrylic acid trimethylolpropane and bis-oxyethylatedbisphenol-A-dimethacrylate.

5. A dental adhesive according to claim 1 or 2, which is used by being polymerized and cured in the presence of a curing agent.

6. A dental adhesive according to claim 5, wherein the curing agent is a combination of a peroxide and an amine compound or a p-toluenesulfinic acid salt.

7. A dental adhesive according to claim 3, which is used by being polymerized and cured in the presence of a curing agent.

8. A dental adhesive according to claim 7, wherein the curing agent is a combination of a peroxide and an amine compound or a p-toluenesulfinic acid salt.

9. The composition of claim 1 having a minimum adhesion strength to bovine tooth dentin of at least 32 kg/cm².

* * * * *